(12) United States Patent
Mavroeidis et al.

(10) Patent No.: US 11,842,268 B2
(45) Date of Patent: Dec. 12, 2023

(54) EVALUATING INPUT DATA USING A DEEP LEARNING ALGORITHM

(71) Applicant: KONINKLIJKE PHILIPS N.V., Eindhoven (NL)

(72) Inventors: Dimitrios Mavroeidis, Utrecht (NL); Monique Hendriks, Eindhoven (NL); Pieter Christiaan Vos, Vught (NL); Sergio Consoli, Nuenen (NL); Jacek Lukasz Kustra, Eindhoven (NL); Johan Janssen, Eindhoven (NL); Ralf Dieter Hoffmann, Brueggen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 487 days.

(21) Appl. No.: 16/648,719

(22) PCT Filed: Sep. 10, 2018

(86) PCT No.: PCT/EP2018/074256
§ 371 (c)(1),
(2) Date: Mar. 19, 2020

(87) PCT Pub. No.: WO2019/057529
PCT Pub. Date: Mar. 28, 2019

(65) Prior Publication Data
US 2020/0251224 A1    Aug. 6, 2020

(30) Foreign Application Priority Data

Sep. 20, 2017   (EP) .................................... 17192217

(51) Int. Cl.
*G06N 3/08* (2023.01)
*G16H 10/60* (2018.01)
(Continued)

(52) U.S. Cl.
CPC ............... *G06N 3/08* (2013.01); *G06F 17/18* (2013.01); *G06F 18/214* (2023.01);
(Continued)

(58) Field of Classification Search
CPC ........ G16H 50/70; G16H 10/60; G06N 20/00; G06N 3/08; G06F 17/18; G06K 9/6223; G06K 9/6256
See application file for complete search history.

(56) References Cited

U.S. PATENT DOCUMENTS

| 4,829,294 | A | * | 5/1989 | Iwami ...................... | G09G 5/14 |
| | | | | | 715/204 |
| 4,962,475 | A | * | 10/1990 | Hernandez ............... | G09G 5/14 |
| | | | | | 345/686 |

(Continued)

FOREIGN PATENT DOCUMENTS

| AU | 2016201298 A1 | 9/2017 |
| WO | 2016094330 A2 | 6/2016 |

OTHER PUBLICATIONS

Guo, et al., "Deformable MR Prostate Segmentation via Deep Feature Learning and Sparse Patch Matching", IEEE Transactions on Medical Imaging, vol. 35, No. 4, Apr. 1, 2016, pp. 1077-1089.
(Continued)

*Primary Examiner* — Nicholas Augustine
(74) *Attorney, Agent, or Firm* — Sherry Austin

(57) ABSTRACT

The invention provides a method for evaluating a set of input data, the input data comprising at least one of: clinical data of a subject; genomic data of a subject; clinical data of a plurality of subjects; and genomic data of a plurality of subjects, using a deep learning algorithm. The method includes obtaining a set of input data, wherein the set of input data comprises raw data arranged into a plurality of data clusters and tuning the deep learning algorithm based on the plurality of data clusters. The deep learning algorithm (Continued)

comprises: an input layer; an output layer; and a plurality of hidden layers. The method further includes performing statistical clustering on the raw data using the deep learning algorithm, thereby generating statistical clusters and obtaining a marker from each statistical cluster. Finally, the set of input data is evaluated based on the markers to derive data of medical relevance in respect of the subject or subjects.

13 Claims, 3 Drawing Sheets

(51) Int. Cl.
| | | |
|---|---|---|
| *G16H 50/70* | (2018.01) | |
| *G06N 20/00* | (2019.01) | |
| *G06F 17/18* | (2006.01) | |
| *G06F 18/214* | (2023.01) | |
| *G06F 18/23213* | (2023.01) | |

(52) U.S. Cl.
CPC ....... *G06F 18/23213* (2023.01); *G06N 20/00* (2019.01); *G16H 10/60* (2018.01); *G16H 50/70* (2018.01)

(56) References Cited

U.S. PATENT DOCUMENTS

| | | | | |
|---|---|---|---|---|
| 5,367,619 | A * | 11/1994 | Dipaolo | G06F 3/0489 715/825 |
| 5,640,577 | A * | 6/1997 | Scharmer | G06F 40/174 715/808 |
| 5,823,948 | A * | 10/1998 | Ross, Jr. | G16H 10/60 600/300 |
| 5,845,255 | A * | 12/1998 | Mayaud | G16Z 99/00 705/3 |
| 5,963,952 | A * | 10/1999 | Smith | G06F 40/123 707/999.102 |
| 6,006,240 | A * | 12/1999 | Handley | G06V 30/412 715/220 |
| 6,112,215 | A * | 8/2000 | Kaply | G06F 3/04895 715/810 |
| 6,192,380 | B1 * | 2/2001 | Light | G06F 40/174 707/999.009 |
| 6,910,179 | B1 * | 6/2005 | Pennell | G06Q 20/108 705/26.8 |
| 6,981,001 | B1 * | 12/2005 | Reddick | G06F 16/9537 |
| 8,788,444 | B2 | 7/2014 | Ball et al. | |
| 2004/0076984 | A1 | 4/2004 | Eils | |
| 2005/0086201 | A1 * | 4/2005 | Weddeling | G06F 8/38 |
| 2006/0010098 | A1 * | 1/2006 | Goodnow | G16H 15/00 |
| 2006/0265249 | A1 * | 11/2006 | Follis | G16H 10/60 715/254 |
| 2008/0244453 | A1 * | 10/2008 | Cafer | G06F 3/04817 715/835 |
| 2011/0125528 | A1 * | 5/2011 | Padate | G16H 10/60 705/3 |
| 2014/0336950 | A1 | 11/2014 | Zhang | |
| 2018/0001184 | A1 * | 1/2018 | Tran | G16H 50/20 |

OTHER PUBLICATIONS

Mamoshina, et al., "Applications of Deep Learning in Biomedicine", Molecular Pharmaceutics, vol. 13, No. 5, Mar. 23, 2016, pp. 1445-1454.

Cole, et al., "Predicting brain age with deep learning from raw imaging data results in a reliable and heritable biomarker", NeuroImage, vol. 163, Jul. 29, 2017, pp. 115-124.

Putin, et al., "Deep biomarkers of human again: Application of deep neural networks to biomarker development", Aging, vol. 8, No. 5, May 18, 2016, pp. 1021-1030.

Xie, et al., "Unsupervised Deep Embedding for Clustering Analysis", May 26, 2016, Retrieved from the Internet: URL:https://arxiv.org/pdf/1511.06335.pdf,[retrieved on Feb. 16, 2018], 10 pages.

Yang, et al., "Towards K-means-friendly Spaces: Simultaneous Deep Learning and Clustering", Jun. 13, 2017, Retrieved from the Internet: URL:https://arxiv.org/pdf/1610.04794.pdf, [retrieved on Feb. 19, 2018], 14 pages.

International Search Report and Written Opinion for International Application No. PCT/EP2018/074256, filed Sep. 10, 2018, 21 pages.

Danaee, et a., "A Deep Learning Approach for Cancer Detection and Relevant Gene Identification", Pacific Symposium on Biocomputing 2017, pp. 219-229.

\* cited by examiner

EVALUATING INPUT DATA USING A DEEP LEARNING ALGORITHM

RELATED APPLICATIONS

This application is the U.S. National Phase application under 35 U.S.C. § 371 of International Application No. PCT/EP2018/074256, filed on Sep. 10, 2018, which claims the benefit of and priority to European Application No. 17192217.2, Sep. 20, 2017. These applications are incorporated by reference herein.

FIELD OF THE INVENTION

This invention relates to the field of deep learning, and more specifically to the field of evaluating subject data using deep learning algorithms.

BACKGROUND OF THE INVENTION

Deep Learning is a branch of machine learning that has recently proved to be very successful in the domains of image analysis, speech recognition and natural language processing. Deep learning algorithms model the nonlinear structures in the input data using a sequence of consecutive layers of non-linear transformations. Although they have become popular only recently due to their success in image and speech analysis tasks, they were originally introduced several decades ago in the machine learning literature. These algorithms are mostly successful in tasks where a large number of training labels is available and feature-engineering often requires a large amount of effort from a domain-expert.

In machine learning the quality and number of the training labels can significantly affect the algorithm's performance. Moreover, in many practical applications, the labelling process typically requires substantial effort by domain experts. Thus, there is a natural motivation to optimize this process and label only the data-instances that are critical to optimize the performance of the machine learning algorithm. Active learning focuses on this problem and guides the learning process such that the most informative data-instances are labelled. In the context of deep learning this problem is very challenging due to the complex optimization process that these algorithms employ.

Deep learning methods rely mostly on optimizing certain supervised (classification) loss-functions and, as discussed above, are successful in cases where a large number of training data is available.

There is therefore a need for a means of training a deep learning algorithm to produce consistently accurate results in the absence of a large set of labelled training data. In addition, there is also a need for a means of obtaining user input regarding the progress of deep learning algorithm without requiring extensive effort on the user's part.

SUMMARY OF THE INVENTION

The invention is defined by the claims.

According to examples in accordance with an aspect of the invention, there is provided a computer-implemented method for evaluating a set of input data, the input data comprising at least one of: clinical data of a subject; genomic data of a subject; clinical data of a plurality of subjects; and genomic data of a plurality of subjects, using a deep learning algorithm, the method comprising:

obtaining a set of input data, wherein the set of input data comprises raw data arranged into a plurality of data clusters;

tuning the deep learning algorithm based on the plurality of data clusters, wherein the deep learning algorithm comprises:
an input layer;
an output layer; and
a plurality of hidden layers;

performing statistical clustering on the raw data using the deep learning algorithm, thereby generating statistical clusters;

obtaining a marker from each statistical cluster, wherein each marker is a biomarker relating to a single clinical parameter contained within a cluster; and evaluating the set of input data based on the markers to derive data of medical relevance in respect of the subject or subjects, wherein the markers are evaluated with reference to historical subject data collected from subjects with similar conditions and/or symptoms to determine a survival rate and/or an effective treatment method for the subject.

This method evaluates a set of input subject data in order to derive data of medical relevance to the subject using a tuned deep learning algorithm. The deep learning algorithm is tuned based on the existing data clusters of the input data in order to increase the accuracy of the deep learning algorithm. By tuning the algorithm based on the input data, for example, the clinical and genomic data of a subject, the deep learning algorithm may more accurately perform the statistical clustering of the raw data.

Markers are obtained from each statistical cluster and used to evaluate the input data in order to derive data of medical relevance to the subject, for example, a survival rate. The markers may be principal variables of the statistical clusters, used to represent the data contained with said statistical cluster.

The markers may be evaluated with reference to historical subject data collected from subjects with similar conditions and/or symptoms.

In some embodiments, the tuning of the deep learning algorithm comprises of:
determining a Gaussian mean width of the input data;
determining a convergence rate of a loss-function of the deep learning algorithm; and
selecting the number of hidden layers based on the Gaussian mean width and the convergence rate.

In this way, the deep learning algorithm is tuned to account for the manifold structure of the input data in addition to the loss-function of the deep learning algorithm. Thus, optimal number of hidden layers is selected and the accuracy of the deep learning algorithm, and so the evaluation of the input data, is increased.

In further embodiments, the computing of the Gaussian width is based on at least one of the size of the data clusters and the number of data clusters.

In this way, the number of hidden layers of the deep learning algorithm may be selected based on the manifold structure of the input data, thereby further increasing the accuracy of the deep learning algorithm.

In an arrangement, the deep learning algorithm is an autoencoder.

In this way, the deep learning algorithm may perform unsupervised learning on the set of input data in order to learn a representation for the set of input data. By employing an autoencoder, a user is not required to supervise and provide feedback on the learning process of the deep learning algorithm.

In some arrangements, the performing of the statistical clustering comprises considering the hidden layers of the deep learning algorithm as low dimensional representations.

In this way, the hidden layers may be represented using a set of principal variables, thereby reducing the processing power required to operate the deep learning algorithm on the set of input data.

In an embodiment, the statistical clustering is k-means clustering.

By performing k-means clustering on the raw data, k statistical clusters may be generated to group the raw data points according their position in data space. In this way, it is possible to quickly and efficiently group similar data points.

In an arrangement, the evaluating of the set of input data comprises predicting a survival rate of the subject.

The markers obtained from the statistical clusters may be used to predict the survival rate of the subject by comparing said markers to data collected from previous subjects having similar conditions and/or symptoms.

In an embodiment, the statistical clustering is performed between adjacent hidden layers of the deep learning algorithm.

By using adjacent layers one can identify different structures of clusters that are related to a hierarchical arrangement of data groups. For example, in a cancer class hierarchy, a high level cluster structure can contain two groups one with cancer subjects and the other with the healthy subjects; whereas, more detailed cluster structures may contain each cancer type in a different cluster. It is known that the architecture of deep learning algorithms can capture such hierarchical relations with layers closer to the input data being related to more general structures while deeper layers can capture the more detailed cluster relations.

In an embodiment, the method further comprises:
identifying an instance pair in the statistical clusters, wherein the instance pair comprises a pair of raw data points belonging to:
different data clusters in the set of input data; and
the same statistical cluster after performing the statistical clustering;
ranking the instance pair according to an angle between the pair of data points in the input data;
presenting the instance pair to a user;
obtaining a user input from the user, indicating whether the instance pair should be clustered together; and
tuning the deep learning algorithm based on the user input.

An instance pair is a borderline case, where two raw data points were originally clustered into different data clusters when using a closer-to-the-input hidden layer but have been brought into the same statistical cluster when using a deeper hidden layer, for example, by way of k-means clustering.

The angle between the instance pairs, as the raw data may be represented in vector form in the data space, may be used to determine a measure of pairing likelihood. In other words, the greater the angle between two data points, the less likely they will be paired together. Following this, instance pairs having a low angle may be automatically accepted as being correctly clustered together; however, for instance pairs having an angle above a predetermined threshold, a user may be required to confirm that the pairing is correct.

By obtaining input from the user on the borderline pairing cases, and tuning the deep learning algorithm based on said user input, the algorithm may be trained to more accurately cluster and interpret the input data. This in turn leads to a more accurate evaluation of the input data to derive medically relevant information relating to the subject.

In a further embodiment, a threshold to the angle is used to limit the number of instance pairs presented to the user. For example, considering the case with multiple instance pairs that exhibit the previously described behavior (originally clustered into different data clusters when using a closer-to-the-input hidden layer and brought into the same statistical cluster when using a deeper hidden layer) with their angles belonging within the range $[0, \pi]$. A threshold may be set at $2\pi/3$, meaning only the instance pairs that have angles above this threshold are displayed to the user. Alternatively, the threshold may be set at any angle in the range $[0, \pi]$.

In this way, it is possible to ensure that the user is not exposed to an unmanageable amount of data and is only presented with instance pairs having the greatest impact on the tuning of the deep learning algorithm.

According to examples in accordance with an aspect of the invention, there is provided a computer program comprising computer program code means which is adapted, when said computer program is run on a computer, to implement the method described above.

According to examples in accordance with an aspect of the invention, there is provided a controller for controlling the evaluation of a set of input data using a deep learning algorithm, wherein the controller is adapted to:
obtain a set of input data, wherein the set of input data comprises raw data arranged into a plurality of data clusters, the input data comprising at least one of: clinical data of a subject; genomic data of a subject; clinical data of a plurality of subjects; and genomic data of a plurality of subjects;
tune the deep learning algorithm based on the plurality of data clusters, wherein the deep learning algorithm comprises:
an input layer;
an output layer; and
a plurality of hidden layers;
perform statistical clustering on the raw data using the deep learning algorithm, thereby generating statistical clusters;
obtain a marker from each statistical cluster, wherein each marker is a biomarker relating to a single clinical parameter contained within a cluster; and evaluate the set of input data based on the markers, wherein the markers are evaluated with reference to historical subject data collected from subjects with similar conditions and/or symptoms to determine a survival rate and/or an effective treatment method for the subject.

In an embodiment, the controller is further adapted to:
compute a Gaussian mean width of the input data;
compute a convergence rate of a loss-function of the deep learning algorithm; and
select the number of hidden layers based on the Gaussian mean width and the convergence rate.

In an arrangement, the controller is further adapted to:
identify an instance pair in the statistical clusters, wherein the instance pair comprises a pair of raw data belonging to:
different data clusters in the set of input data; and
the same statistical cluster after performing the statistical clustering;
rank the instance pair according to an angle between the pair of data points in the input data;

for an instance pair having an angle greater than a predetermined value, present the instance pair to a user;
obtain a user input from the user, indicating whether the instance pair should be clustered together; and
tune the deep learning algorithm based on the user input.

According to examples in accordance with an aspect of the invention, there is provided a data analysis system, the system comprising:
a storage device, adapted to store the input data;
the controller as described above in communication with the storage device;
a user interface, adapted to obtain a user input, in communication with the controller; and
a display device, adapted to display information to a user, in communication with the controller.

According to yet a further aspect of the invention there is provided a method for evaluating a set of input data, the input data comprising at least one of: clinical data of a subject; genomic data of a subject; clinical data of a plurality of subjects; and genomic data of a plurality of subjects, using a deep learning algorithm, the method comprising:
obtaining a set of input data, wherein the set of input data comprises raw data arranged into a plurality of data clusters;
tuning the deep learning algorithm based on the plurality of data clusters, wherein the deep learning algorithm comprises: an input layer; an output layer; and a plurality of hidden layers;
performing statistical clustering on the raw data using the deep learning algorithm, thereby generating statistical clusters;
obtaining a marker from each statistical cluster; and
evaluating the set of input data based on the markers to derive data of medical relevance in respect of the subject.

According to yet a further aspect of the invention there is provided a controller for controlling the evaluation of a set of input data using a deep learning algorithm, wherein the controller is adapted to:
obtain a set of input data, wherein the set of input data comprises raw data arranged into a plurality of data clusters;
tune the deep learning algorithm based on the plurality of data clusters, wherein the deep learning algorithm comprises: an input layer; an output layer; and a plurality of hidden layers;
perform statistical clustering on the raw data using the deep learning algorithm, thereby generating statistical clusters;
obtain a marker from each statistical cluster; and
evaluate the set of input data based on the markers.

These and other aspects of the invention will be apparent from and elucidated with reference to the embodiment(s) described hereinafter.

BRIEF DESCRIPTION OF THE DRAWINGS

Examples of the invention will now be described in detail with reference to the accompanying drawings, in which.

DETAILED DESCRIPTION OF THE EMBODIMENTS

Embodiments of the invention provides a method for evaluating a set of input data, the input data comprising at least one of: clinical data of a subject; genomic data of a subject; clinical data of a plurality of subjects; and genomic data of a plurality of subjects, using a deep learning algorithm. The method includes obtaining a set of input data, wherein the set of input data comprises raw data arranged into a plurality of data clusters and tuning the deep learning algorithm based on the plurality of data clusters. The deep learning algorithm comprises: an input layer; an output layer; and a plurality of hidden layers. The method further includes performing statistical clustering on the raw data using the deep learning algorithm, thereby generating statistical clusters and obtaining a marker from each statistical cluster. Finally, the set of input data is evaluated based on the markers to derive data of medical relevance in respect of the subject or subjects.

Figure 1:
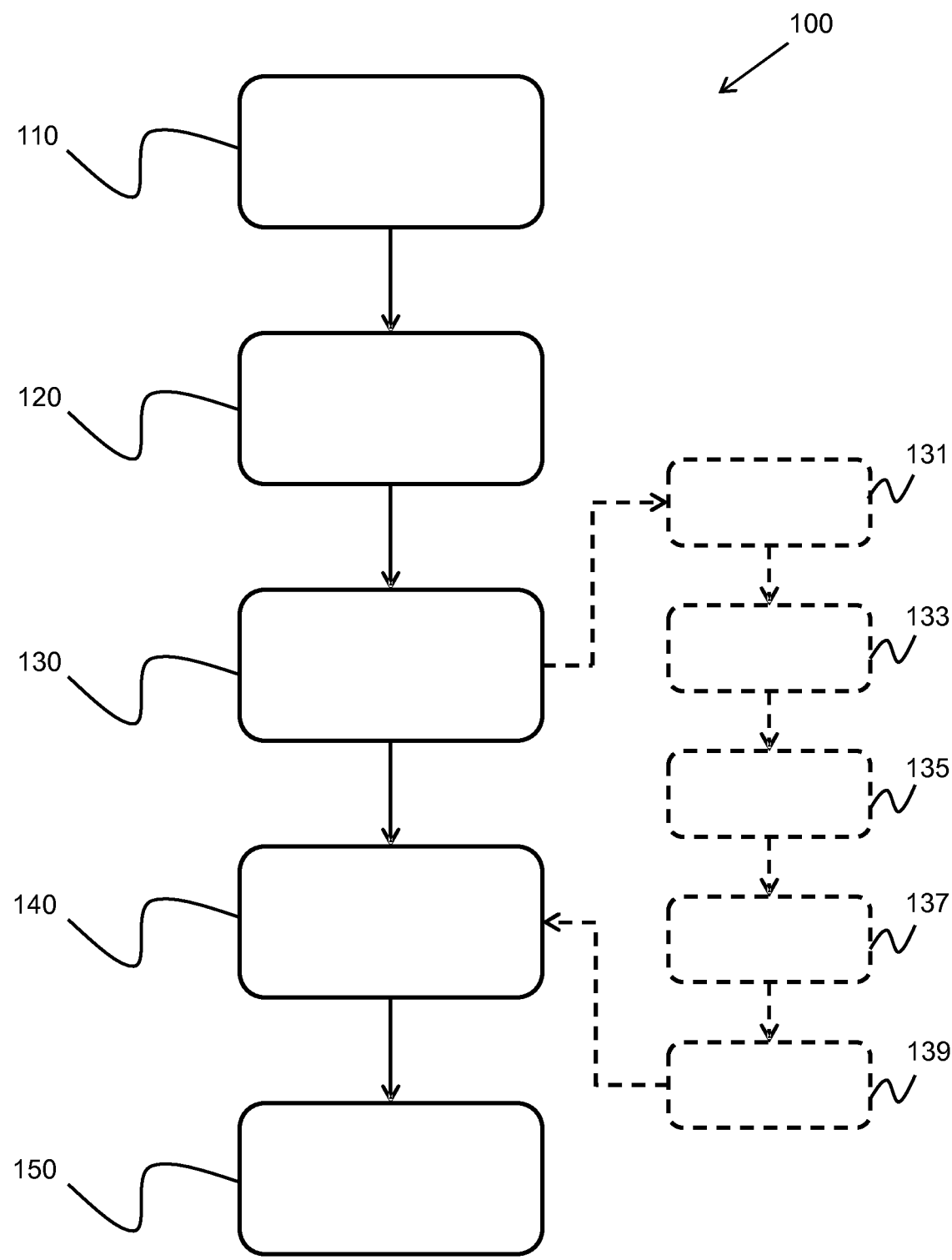
FIG. 1 shows a method of the invention.

FIG. 1 shows a method 100 of evaluating a set of subject input data using a deep learning algorithm.

In step 110, a set of input data is obtained. The input data comprises raw data arranged into a plurality of data clusters. The raw data may comprise clinical and genomic data of a subject, or plurality of subjects, to be evaluated to derive medically significant data regarding the subject, or subjects.

For example, the data may be evaluated to determine a survival rate of a subject by evaluating the subject's data against a plurality of subjects having the same symptoms or conditions. The raw subject data may, for example, comprise: subject age; blood test results; symptoms; previously diagnosed conditions; and the like.

In step 120, the deep learning algorithm is tuned based on the plurality of data clusters of the set of input data, wherein the deep learning algorithm comprises: an input layer; an output layer; and a plurality of hidden layers.

The tuning of the deep learning algorithm may comprise: determining a Gaussian mean width of the input data; determining a convergence rate of a loss-function of the deep learning algorithm; and selecting the number of hidden layers based on the Gaussian mean width and the convergence rate. The computing of the Gaussian width may be based on the size of the data clusters and/or the number of data clusters.

Gaussian mean width is formally defined as $E[\sup_{x,y \in K} <g, x-y>]$, where g is a standard Gaussian random variable. Intuitively, it provides a measure of size of set K and can be computed for certain frequently used data distribution models, such as: a mixture of Gaussians; sparse signals represented by a dictionary basis; and the like.

In some cases, formulas for a mixture of Gaussians or a sparse dictionary structure may be used to determine several Gaussian mean widths for a given set of input data. The final choice of which Gaussian mean width to use for tuning the deep learning algorithm may be made based on the associated convergence rate for each width.

The deep learning algorithm can be trained with several different architecture choices and the convergence rate of the loss function can be used as a criterion to select the optimal one, with faster convergence signifying the better architecture.

In step 130, statistical clustering is performed on the raw data using the deep learning algorithm, thereby generating statistical clusters. The statistical clustering may consider the hidden layers of the deep learning algorithm as low dimensional representations. In other words, principal variables of the hidden layers may be identified to perform the statistical clustering in order to reduce the number of computations required.

The statistical clustering method may, for example, be k-means clustering. K-means clustering is a method of vector quantization, which models a probability density function based on the distribution of vectors, such as the input data. The k-means clustering groups the input data into k different clusters.

Given a set of raw data $(x_1, x_2, \ldots, x_n)$, where each data point is a d-dimensional real vector, k-means clustering aims to partition the n data points into k, where k≤n, sets $S=\{S_1, S_2, \ldots, S_k\}$ so as to minimize the within-cluster sum of squares (WCSS) i.e. the variance. Formally, the objective is to find:

$$\operatorname*{argmin}_{S} \sum_{i=1}^{k} \sum_{x \in S_i} \|x - \mu_i\|^2 = \operatorname*{argmin}_{S} \sum_{i=1}^{k} |S_i| \operatorname{Var} S_i,$$

where $\mu_i$ is the mean of the data points in set $S_i$.

The statistical clustering may be performed between adjacent hidden layers of the deep learning algorithm. By using adjacent layers one can identify different cluster structures that are related to a hierarchical arrangement of data groups. For example, in a cancer class hierarchy, a high level cluster structure can contain two groups one with cancer subjects and the other with the healthy subjects; whereas, more detailed cluster structures may contain each cancer type in a different cluster. It is known that the architecture of deep learning algorithms can capture such hierarchical relations with layers closer to the input data being related to more general structures while deeper layers can capture the more detailed cluster relations.

Following the statistical clustering performed in step 130, the method may include several additional steps for tuning the deep learning algorithm.

In step 131, an instance pair is identified within the statistical clusters. An instance pair is defined as a pair of raw data points belonging to different data clusters in the original set of input data and the same statistical cluster after performing the statistical clustering.

In step 133, the instance pair may be ranked according to an angle between the pair of data points in the input data. The angle can be measured using the vector representation induced by each network layer.

In step 135, for an instance pair having an angle greater than a threshold angle, the instance pair may be presented to a user. A threshold to the angles can be set to limit the amount of data that a user is exposed to. For example, considering the case with multiple instance pairs that exhibit the previously described behavior (originally clustered into different data clusters when using a closer-to-the-input hidden layer and brought into the same statistical cluster when using a deeper hidden layer) with their angles belonging within the range [0, π]. A threshold may be set at 2π/3, meaning only the instance pairs that have angles above this threshold are displayed to the user. Alternatively, the threshold may be set at any angle in the range [0, π].

In step 137, a user input may be obtained from the user, indicating whether the instance pair should be clustered together.

For instance pairs that are considered to be unlikely to be paired together, based on their angle in the input data set, the user may provide an input indicating whether the pairing is correct or not. In this way, the deep learning algorithm may also receive supervised input from a trained user in order to increase the accuracy of the algorithm.

In step 139, the deep learning algorithm may be tuned based on the user input.

By tuning the deep learning algorithm based on the user input, the deep learning algorithm may more accurately assess similar instance pairs in future method cycles, without necessarily requiring additional input from the user. In this way, the deep learning algorithm is made more accurate and efficient.

In step 140, a marker is obtained from each statistical cluster produced by the deep learning algorithm. As the input data comprises the clinical and/or genomic data of a subject, or plurality of subjects, the markers may be biomarkers relating to a single clinical parameter contained within a given cluster.

The markers may be compared against historic subject records in order to determine which markers have previously served as important subject evaluation points. In this way, the deep learning algorithm may be trained to preferentially identify and evaluate these evaluation points. This is particularly important in cases where only a small amount of data is available for a subject or when the input data is largely unlabeled.

In step 150, the set of input data is evaluated based on the markers to derive data of medical relevance in respect of the subject or subjects The markers may be evaluated to derive medically relevant data of a subject, for example, a survival rate of the subject. The survival rate of the subject may be evaluated by comparing the markers to historical data collected from other subjects with similar conditions and/or symptoms. Alternatively, the historic subject data may also include various treatment methods and their effectiveness at treating the known conditions. In this way, the evaluation may also indicate an effective treatment method for the condition of the subject.

Figure 2:
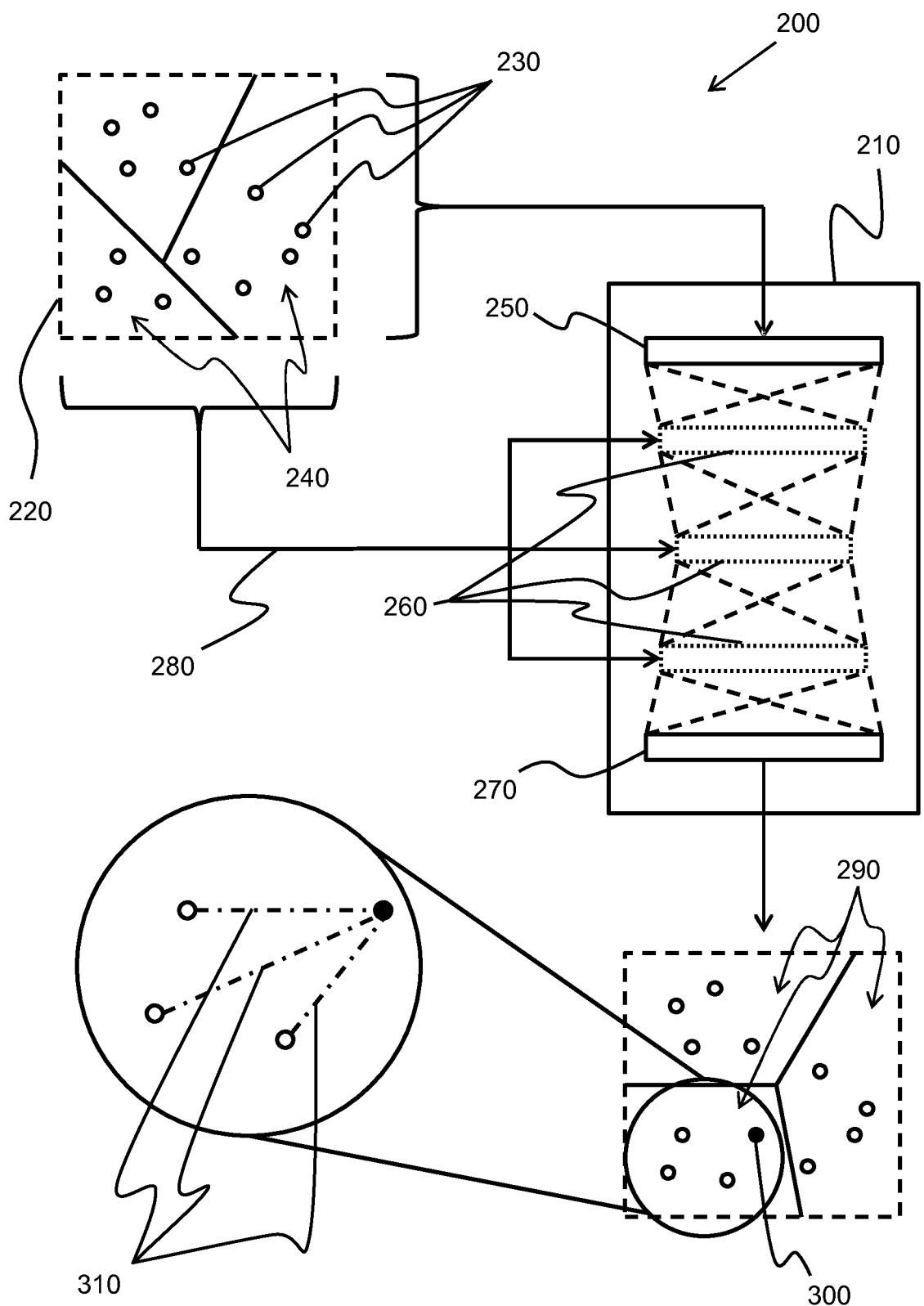
FIG. 2 shows a visual representation of an autoencoder operating on a set of input data.

FIG. 2 shows a visual representation 200 of an autoencoder 210 performing k-means clustering on a set of input data 220. It can be seen that the input data 220 comprises raw data points 230 arranged into a plurality of data clusters 240, represented on a Voronoi diagram.

In this example, the deep learning algorithm is an autoencoder 210. An autoencoder is an artificial neural network that may be used for unsupervised feature learning. The autoencoder comprises: an input layer 250; a plurality of hidden layers 260; and an output layer 270.

As described above, the hidden layers 260 of the autoencoder 210 are tuned 280 based on the input data. For example, in this case, as there are three data clusters in the original input data, the number of hidden layers of the autoencoder is set to three. Alternatively, the hidden layers may be tuned based on the size of each of the data clusters.

Following the tuning of the autoencoder, the raw data 230 is passed to the input layer 250. The raw data is then passed through the hidden layers 260 to the output layer 270. The output layer has the same number of nodes as the input layer and so simply acts to reconstruct the raw data into new statistical clusters 290.

In this example, the statistical clusters 290 are largely similar to the data clusters 240 of the input data 220; however, it can be seen that one data point 300 has changed cluster. This data point forms instance pairs 310 with the other data points in the new cluster. These instance pairs may then be ranked according to the angles between the data points in the original data points in the input data set. Those instance pairs above a given threshold angle may be presented to a user in order to obtain user feedback on whether the new clustering of these data points is correct. The autoencoder may then be tuned based on the user's feedback.

Figure 3:
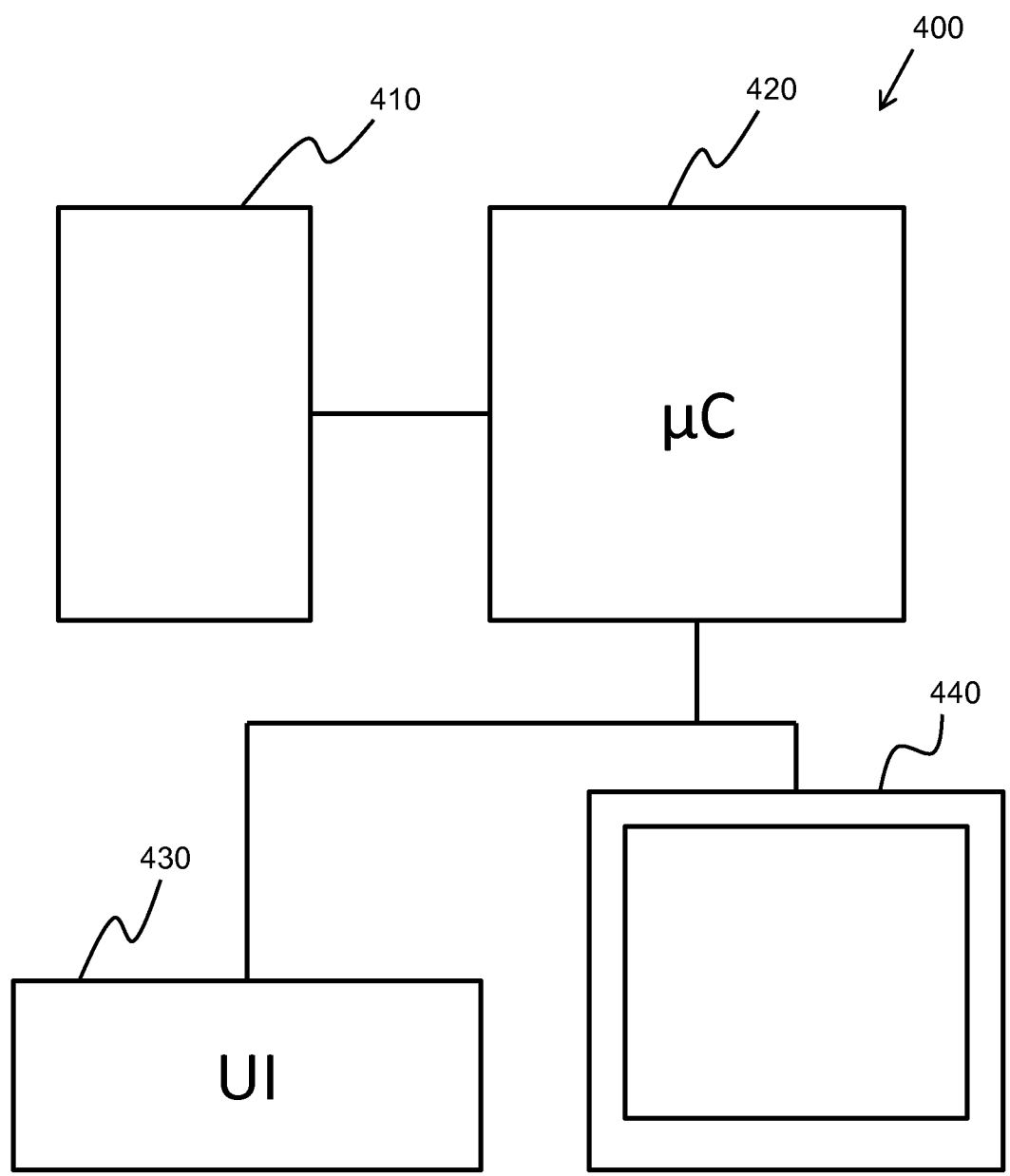
FIG. 3 shows a data analysis system for executing the method of FIG. 1.

FIG. 3 shows an example of a data analysis system 400. The data analysis system comprises: a storage device 410, adapted to store the input data; a controller 420 in communication with the storage device; a user interface 430, adapted to obtain a user input, in communication with the controller; and a display device 440, adapted to display information to a user, in communication with the controller.

As discussed above, embodiments make use of a controller 420 for performing the data processing steps.

The controller can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media 410 such as volatile and non-volatile computer memory such as RAM, PROM, EPROM, and EEPROM. The storage media may be encoded with one or more programs that, when executed on one or more processors and/or controllers, perform at the required functions. Various storage media may be fixed within a processor or controller or may be transportable, such that the one or more programs stored thereon can be loaded into a processor or controller.

The user interface 430 may comprise: a mouse; a keyboard; or any other suitable means of obtaining a user input. The display device 440 may comprise a screen.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer-implemented method for evaluating a set of input data using a deep learning neural network, the input data comprising at least one of: clinical data of a first subject; genomic data of a second subject; clinical data of a first plurality of subjects; or genomic data of a second plurality of subjects, the method comprising:
   obtaining a set of input data, wherein the set of input data comprises raw data arranged into a plurality of data clusters;
   tuning the deep learning neural network based on the plurality of data clusters, wherein the deep learning neural network comprises:
      an input layer;
      an output layer; and
      a plurality of hidden layers;
   performing statistical clustering on the raw data using the deep learning neural network to generate statistical clusters;
   determining that two raw data points of the raw data are clustered into different data clusters of the plurality of data clusters of the input data;
   determining that the two raw data points are clustered into a same statistical cluster of the statistical clusters;
   categorizing the two raw data points as an instance pair based on the two raw data points being clustered into the different data clusters of the plurality of data clusters of the input data, and being clustered in the same statistical cluster;
   identifying vectors associated with the two raw data points of the instance pair;
   calculating an angle between the vectors;
   when the angle is above a threshold,
      presenting the instance pair to a user;
      obtaining a user input from the user, indicating whether the instance pair should be clustered together; and
      tuning the deep learning neural network based on the user input;
   obtaining a marker from each statistical cluster, wherein each marker is a biomarker relating to a single clinical parameter contained within a cluster of the statistical clusters; and
   evaluating the set of input data based on the markers to derive data of medical relevance to the first subject, the second subject, the first plurality of subjects or the second plurality of subjects, wherein the markers are evaluated with reference to historical subject data collected from subjects with similar conditions and/or symptoms to determine a survival rate and/or an effective treatment method for the first subject, the second subject, the first plurality of subjects or the second plurality of subjects.

2. A method as claimed in claim 1, wherein the tuning of the deep learning neural network comprises:
   determining a Gaussian mean width of the input data;
   determining a convergence rate of a loss-function of the deep learning neural network; and
   selecting a number of hidden layers based on the Gaussian mean width and the convergence rate.

3. A method as claimed in claim 2, wherein the determining of the Gaussian mean width is based on at least one of the size of the plurality of data clusters of the input data and a number of the plurality of data clusters of the input data.

4. A method as claimed in claim 1, wherein the deep learning neural network is an autoencoder.

5. A method as claimed in claim 1, wherein the performing of the statistical clustering comprises considering the hidden layers of the deep learning neural network as low dimensional representations, wherein principal variables of the hidden layers are identified to perform the statistical clustering in order to reduce a number of computations required.

6. A method as claimed in claim 1, wherein the statistical clustering is k-means clustering.

7. A method as claimed in claim 1, wherein the evaluating of the set of input data comprises predicting a survival rate of the first or second subject.

8. A method as claimed in claim 1, wherein the statistical clustering is performed between adjacent hidden layers of the deep learning neural network.

9. A method as claimed in claim 1, wherein the threshold to the angle is used to limit a number of instance pairs presented to the user.

10. A computer program comprising computer program code means which is adapted, when said computer program is run on a computer, to implement the method of claim 1.

11. A controller for controlling an evaluation of a set of input data using a deep learning neural network, wherein the controller is adapted to:
- obtain a set of input data, wherein the set of input data comprises raw data arranged into a plurality of data clusters, the input data comprising at least one of: clinical data of a first subject; genomic data of a second subject; clinical data of a first plurality of subjects; or genomic data of a second plurality of subjects;
- tune the deep learning neural network based on the plurality of data clusters, wherein the deep learning neural network comprises:
  - an input layer;
  - an output layer; and
  - a plurality of hidden layers;
- perform statistical clustering on the raw data using the deep learning neural network to generate statistical clusters;
- determine that two raw data points of the raw data are clustered into different data clusters of the plurality of data clusters of the input data;
- determine that the two raw data points are clustered into a same statistical cluster of the statistical clusters;
- categorize the two raw data points as an instance pair based on the two raw data points being clustered into the different data clusters of the plurality of data clusters of the input data, and being clustered in the same statistical cluster;
- identify vectors associated with the two raw data points of the instance pair;
- calculate an angle between the vectors;
- when the angle is above a threshold,
  - present the instance pair to a user;
  - obtain a user input from the user, indicating whether the instance pair should be clustered together; and
  - tune the deep learning neural network based on the user input;
- obtain a marker from each statistical cluster, wherein each marker is a biomarker relating to a single clinical parameter contained within a cluster of the statistical clusters; and
- evaluate the set of input data based on the markers, wherein the markers are evaluated with reference to historical subject data collected from subjects with similar conditions and/or symptoms to determine a survival rate and/or an effective treatment method for the first subject, the second subject, the first plurality of subjects or the second plurality of subjects.

12. The controller as claimed in claim 11, wherein the controller is further adapted to:
- determine a Gaussian mean width of the input data;
- compute a convergence rate of a loss-function of the deep learning neural network; and
- select a number of hidden layers based on the Gaussian mean width and the convergence rate.

13. A data analysis system, the system comprising:
- a storage device, adapted to store the input data;
- the controller as claimed in claim 11 in communication with the storage device;
- a user interface, adapted to obtain a user input, in communication with the controller; and
- a display device, adapted to display information to a user, in communication with the controller.

* * * * *